(12) United States Patent  
Yu et al.

(10) Patent No.: US 9,360,423 B2
(45) Date of Patent: Jun. 7, 2016

(54) OPTICAL SYSTEM FOR A HOLOGRAPHIC MICROSCOPE INCLUDING A SPATIAL FILTER

(75) Inventors: Chung-Chieh Yu, Tucson, AZ (US); Isao Matsubara, Tochigi (JP); Yasuyuki Unno, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 368 days.

(21) Appl. No.: 13/538,185

(22) Filed: Jun. 29, 2012

(65) Prior Publication Data

US 2013/0003073 A1 Jan. 3, 2013

Related U.S. Application Data

(60) Provisional application No. 61/504,100, filed on Jul. 1, 2011, provisional application No. 61/504,093, filed on Jul. 1, 2011.

(51) Int. Cl.
*G01N 21/45* (2006.01)
*G02B 21/00* (2006.01)
*G03H 1/00* (2006.01)
*G03H 1/04* (2006.01)

(52) U.S. Cl.
CPC ......... *G01N 21/453* (2013.01); *G02B 21/0056* (2013.01); *G03H 1/0005* (2013.01); *G03H 1/0443* (2013.01); *G03H 2001/005* (2013.01); *G03H 2001/0452* (2013.01); *G03H 2223/12* (2013.01); *G03H 2223/22* (2013.01); *G03H 2223/52* (2013.01); *G03H 2223/55* (2013.01)

(58) Field of Classification Search
CPC ............. G01N 21/453; G02B 21/0056; G03H 2223/52; G03H 2223/55; G03H 2001/2207; G03H 1/0005; G03H 1/0443; G03H 2223/12; G01B 9/021
USPC .......................... 356/450, 457, 458, 520, 521
See application file for complete search history.

(56) References Cited

U.S. PATENT DOCUMENTS

| | | | | | |
|---|---|---|---|---|---|
| 5,822,066 | A | * | 10/1998 | Jeong et al. | 356/521 |
| 5,835,217 | A | * | 11/1998 | Medecki | 356/521 |
| 6,100,978 | A | * | 8/2000 | Naulleau et al. | 356/498 |
| 6,118,535 | A | * | 9/2000 | Goldberg et al. | 356/521 |
| 6,307,635 | B1 | * | 10/2001 | Goldberg | 356/521 |
| 6,452,146 | B1 | * | 9/2002 | Barchers | 250/201.9 |
| 6,573,997 | B1 | * | 6/2003 | Goldberg et al. | 356/521 |
| 6,707,560 | B1 | * | 3/2004 | Naulleau et al. | 356/515 |
| 7,057,737 | B2 | | 6/2006 | Millerd et al. | |

(Continued)

OTHER PUBLICATIONS

Balcunas et al., "Tilted-pulse time-resolved off-axis digital holography," Optics Letters, Sep. 15, 2009, pp. 2715-2717, vol. 34, No. 18.

(Continued)

*Primary Examiner* — Michael P Lapage
(74) *Attorney, Agent, or Firm* — Canon USA, Inc. IP Division

(57) ABSTRACT

An optical system for a holographic microscope includes: a light source configured to emit a light beam; a grating configured to split the light beam into a reference beam and an object beam; a lens unit configured to irradiate a sample by the reference and object beams split by the grating; a spatial filter including a first region for the reference beam and a second region for the object beam; and a detector configured to detect an interference pattern caused by the reference and object beams.

14 Claims, 12 Drawing Sheets

(56) References Cited

U.S. PATENT DOCUMENTS

| | | | |
|---|---|---|---|
| 7,106,456 B1* | 9/2006 | Cottrell | 356/521 |
| 7,231,718 B2* | 6/2007 | Outen | 30/161 |
| 2004/0252311 A1* | 12/2004 | Ishii et al. | 356/512 |
| 2005/0046863 A1* | 3/2005 | Millerd et al. | 356/495 |
| 2005/0046865 A1 | 3/2005 | Brock et al. | |
| 2006/0203251 A1* | 9/2006 | Millerd et al. | 356/495 |
| 2007/0211256 A1* | 9/2007 | Medower et al. | 356/491 |
| 2009/0290156 A1 | 11/2009 | Popescu et al. | |

OTHER PUBLICATIONS

Maznev et al., "How to make femtosecond pulses overlap," Optics Letters, Sep. 1, 1998, pp. 1378-1380, vol. 23, No. 17.

Ansari et al., "Elimination of beam walk-off in low-coherence off-axis photorefractive holography," Optics Letters, Mar. 15, 2001, pp. 334-336, vol. 26, No. 6.

Popescu et al., "Diffraction phase microscopy for quantifying cell structure and dynamics," Optics Letters, Mar. 15, 2006, pp. 775-777, vol. 31, No. 6.

Cuche et al., "Spatial Filtering for Zero-Order and Twin-Image Elimination in Digital Off-Axis Holography," Applied Optics, Aug. 10, 2000, pp. 4070-4075, vol. 39, Issue 23.

Zhuo Wang, Larry Millet, Mustafa Mir, Huafeng Ding, Sakulsuk Unarunotai, John Rogers, Martha U. Gillette, Gabriel Popescu, Spatial Light Interference Microscopy (SLIM), Optics Express, Jan. 7, 2011, 19 (2):1017-1026, Optical Society of America, Washington DC, 2011.

* cited by examiner

After polarizer 2

After polarizer 1

Incident light

OPTICAL SYSTEM FOR A HOLOGRAPHIC MICROSCOPE INCLUDING A SPATIAL FILTER

CROSS REFERENCE TO RELATED APPLICATIONS

This application claims priority to U.S. provisional application No. 61/504,100 filed Jul. 1, 2011 entitled "Holographic Microscope", and U.S. provisional application No. 61/504,093 filed Jul. 1, 2011 entitled "Holographic Microscope", of which the entire contents of both are hereby incorporated by reference.

BACKGROUND OF THE INVENTION

1. Field of the Invention

The present invention relates to an optical system for a holographic microscope.

2. Description of the Related Art

Popescu et al. (Optics Letters, v. 31, pages 775-777, 2006 (Diffraction phase microscopy for quantifying cell structure and dynamics)) have developed diffraction phase microscopy, which is shown in FIG. 1, as a technique for quantitative phase imaging of biological structures. The method combines the principles of common path interferometry and single-shot phase imaging and is characterized by subnanometer pathlength stability and millisecond-scale acquisition time. The potential of the technique for quantifying nanoscale motions in live cells is demonstrated by experiments on red blood cells.

An experimental setup is illustrated in FIG. 1. VPS means a virtual source point, RL is a relay lens, G is a grating, IP is an image plane, $L_{1,2}$ are lenses ($f_{1,2}$, respective focal distances), SF means a spatial filter, and CCD is used as a detector.

In this Letter by Popescu et al., they introduce diffraction phase microscopy (DPM) as a novel quantitative phase imaging technique. DPM uses the common path geometry and provides quantitative phase images that are inherently stable to the level of the subnanometer optical path length and at an acquisition speed limited only by the detector.

The second harmonic ($\lambda$=532 nm) radiation of a Nd:YAG laser was used as illumination for an inverted microscope (Axiovert 35, Carl Zeiss, Inc.), which produces a magnified image of the sample at the output port. The microscope image appears to be illuminated by the virtual source point (VPS). The relay lens (RL) was used to collimate the light originating at the VPS and replicate the microscope image at the image plane (IP).

A phase grating G is placed at this image plane (IP), which generates multiple diffraction orders containing full spatial information about the image. They isolate the zeroth and first diffraction orders to be used as sample and reference fields, respectively, similar to typical Mach-Zender interferometry. To accomplish this, a standard spatial filtering lens system $L_1$-$L_2$ is used to select the two diffraction orders and generate the final interferogram at the CCD plane.

The zeroth order beam is low-pass filtered by using the spatial filter (SF) positioned in the Fourier plane of L1, such that at the CCD plane it approaches a uniform field. The spatial filter allows passing the entire frequency content of the first diffraction order beam and blocks all the other orders.

The first order beam is thus the imaging field and the zeroth order beam plays the role of the reference field. The two beams traverse the same optical components, i.e., they propagate along a common optical path, thus significantly reducing the longitudinal phase noise. The direction of the spatial modulation was chosen at an angle of 45° with respect to the x and y axes of the CCD, such that the total field at the CCD plane has the form described in the following equation (1).

$$E(x,y)=|E_O|e^{i[\phi_0+\beta(x+y)]}|E_1(x,y)|e^{i\phi(x,y)} \quad (1)$$

In Eq. (1), $|E_O|$ and $|E_1|$ are the amplitudes, and $\phi_0$ and $\phi$ are the phases of the orders of diffraction 0, 1, respectively, while $\beta$ represents the spatial frequency shift induced by the grating to the zeroth order. Note that, as a consequence of the central ordinate theorem, the reference field is proportional to the spatial average of the microscope image field described below.

$$|E_0|e^{i\phi_0} \propto \frac{1}{A}\int |E_1(x,y)|e^{i\phi(x,y)}dxdy \quad (2)$$

where A is the total image area. The spatial average of an image field has been successfully used before as a stable reference for extracting spatially resolved phase information. The interferogram is spatially high-pass filtered to isolate the cross term, $|E_O||E_1(x,y)|\cos[\phi(x,y)-\beta(x+y)-\phi_0]$. For the transparent objects of interest here, $E_1(x,y)$ is expected to have a weak spatial dependence. The spatially resolved quantitative phase image associated with the sample is retrieved from a single CCD recording via a spatial Hilbert transform.

The efficiency of the grating G depends on the angle of use. On the image plane IP, where the grating is placed illustrated in FIG. 1, the signal beam has wide angular contents which carry the information of interest. Therefore, the grating will modify the angular contents of the signal; thus, may change the image of the object under investigation.

SUMMARY OF THE INVENTION

Embodiments of the present invention provide an optical system for a holographic microscope.

According to an aspect of the present invention, it is provided that an optical system for a holographic microscope includes: a light source configured to emit a light beam; a grating configured to split the light beam into a reference beam and an object beam; a lens unit configured to irradiate a sample by the reference and object beams split by the grating; a spatial filter including a first region for the reference beam and a second region for the object beam; and a detector configured to detect an interference pattern caused by the reference and object beams.

According to another aspect of the present invention, it is provided that an optical system for a holographic microscope includes: a light source configured to emit a light beam to irradiate a sample; a beam splitter configured to split the light beam which has gone through the sample into a reference beam and an object beam; a spatial filter including a first region and a second region, the reference beam going through the first region; a grating configured to refract the reference beam so that the reference beam goes through the second region of the spatial filter; and a detector configured to detect an interference pattern caused by the reference beam, which has gone through the second region of the spatial filter, and the object beam.

According to another aspect of the present invention, it is provided that an optical system for a holographic microscope includes: a light source configured to emit a light beam; a spatial filter including a first region for an object beam and a second region for a reference beam; a first polarizer for the object beam which has gone through the first region of the spatial filter; a second polarizer configured to interfere the object beam with the reference beam; and a detector configured to detect an interference pattern caused by the reference and object beams.

Further features of the present invention will become apparent from the following description of exemplary embodiments with reference to the attached drawings.

DESCRIPTION OF THE EMBODIMENTS

Embodiments according to the present invention will be described below with reference to the attached drawings.

First Embodiment

In a first embodiment, an optical system for off-axis holography with common path approach is described.

In traditional holography, two beams are required. One is the reference beam which does not go through the sample. Another one is the object beam which goes through the sample and carries sample information induced by the sample. Usually, two beams are separated using a beam splitter, and the reference beam and object beam are set up similarly along two different light paths. The drawback for this type of arrangement is that the two light paths may experience different disturbance which causes noise on the holograms. Another significant shortcoming is for implementing holography in microscopy. When the object beam goes through the sample or is reflected from the sample and then goes through the objective lens, it might be difficult to match the light field curvature of the reference beam with that of the object beam because an objective lens is frequently changed to have a wide range of field of view and resolution. Therefore, a common path (i.e., the object beam and reference beam go through substantially the same light path or light paths very close to each other) approach is desirable.

Figure 2:
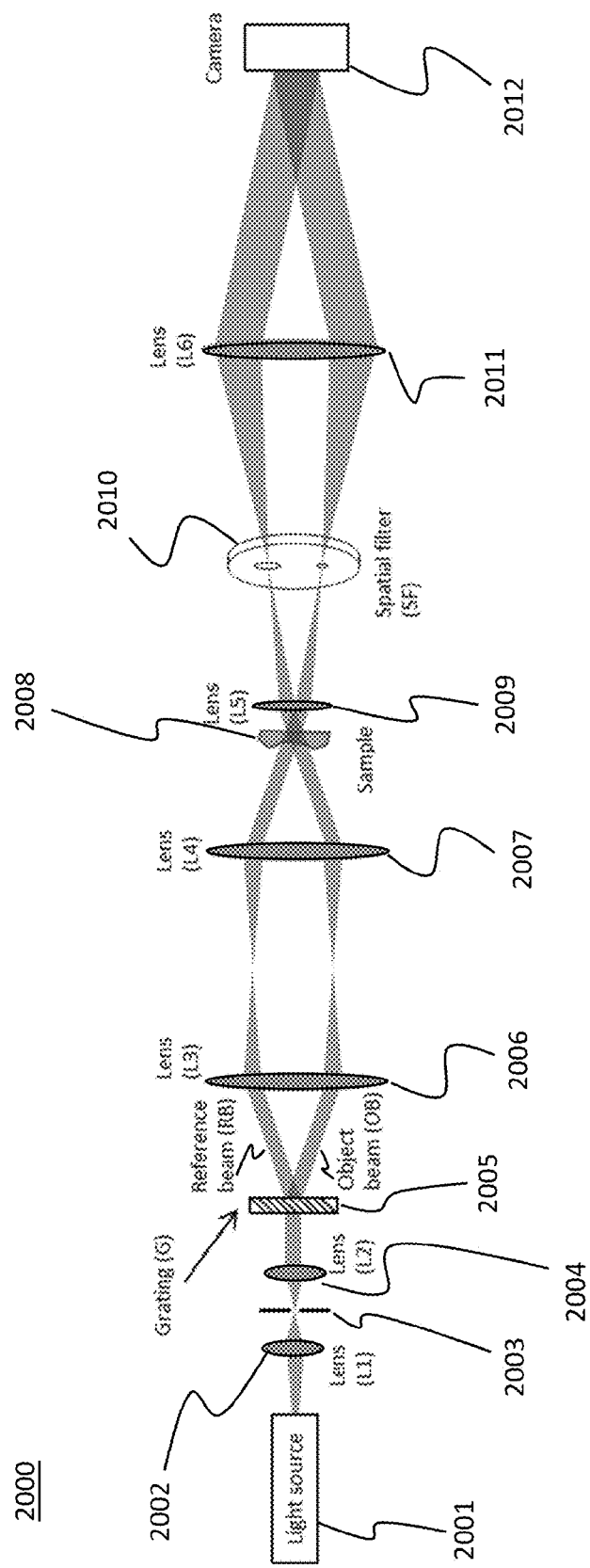
FIG. 2 illustrates an optical system of a first embodiment.

A diagram of an optical system 2000 for a holographic microscope, with common-path off-axis holography, is illustrated in FIG. 2. The light beam from a light source 2001 goes through a lens (L1) 2002 and a pinhole 2003 and is then collimated by a lens (L2) 2004, to form a plane wave.

Two beams, a reference beam (RB) and an object beam (OB), are split by the grating (G) 2005. For the traditional holographic system, the RB and the OB have two different beam path lengths and their phase fronts are usually not parallel to each other in the off-axis configuration. Splitting the light beam using the grating 2005 enables the optical system presented in FIG. 2 to have the phase fronts of both RB and OB parallel on the camera 2012 and the difference between beam path lengths can be very small.

The reference and object beams go through a lens (L3) 2006, a lens (L4) 2007, and a sample 2008. The two lenses 2009 and 2011 (L5 and L6) form a 4-f relay lens system which images the sample 2008 onto the camera 2012 as a detector.

Both the reference beam (RB) and object beam (OB) have the spatial information about the sample after they go through the sample 2008. However, when the reference beam goes through the spatial filter (SF) 2010, which is positioned at the Fourier plane, the sample information carried by the high spatial frequency components is blocked by the smaller pinhole of SF 2010 and only the DC component is through the pinhole of the size of the Airy diameter. (The DC component means spatially homogeneous light, such as a plane wave.) Since the object beam goes through the bigger pinhole of SF 2010 which allows the spatial frequency contents to go through, the object beam still carries the information induced by the sample 2008.

Electric fields for an object beam, $E_O(x,y)$, and a reference beam, $E_R(x,y)$, after the sample can be written as follows:

$$E_O(x,y)=E_y(x,y)\exp[i\phi(x,y)]$$

$$E_R(x,y)=E_x(x,y)\exp[i(\phi(x,y)+\beta y)] \quad (3)$$

After the spatial filter, the electric fields can be written as follows:

$$E_O(x,y)=E_y(x,y)\exp[i\phi(x,y)]$$

$$E_R(x,y)=E_x(x,y)\exp[i(\beta y+\phi(0,0))] \quad (4)$$

When two beams are recombined on the camera 2012, the light intensity on the detector is expressed as $$|E_O(x,y)+E_R(x,y)|^2=|E_O(x,y)|^2+|E_R(x,y)|^2+E_O(x,y)E_R^*(x,y)+E_O^*(x,y)E_R(x,y) \quad (5)$$

where the first and second terms correspond to 0th order light, and the third term corresponds to +1st order light, and the fourth term corresponds to −1st order light. The sample information is recorded in the +1st and −1st order lights.

The third and fourth terms, which are an important part for intensity on the detector, can be re-written as follows.

$$E_O(x, y)E_R^* + E_O^*(x, y)E_R = \quad (6)$$
$$|E_O(x, y)||E_R|(\exp[i(\phi(x, y) - \beta y - \phi(0, 0))] +$$
$$\exp[-i(\phi_O(x, y) - \beta y - \phi(0, 0))]) =$$
$$2|E_O(x, y)||E_R|\cos(\phi(x, y) - \beta y - \phi(0, 0))$$

Moreover, the same distribution can be obtained by calculating a real part of the third term.

Note that Eq. (6) is basically the same as the cross term, $|E_O||E_1(x,y)|\cos[\phi(x,y)-\beta(x+y)-\phi_o]$, in the related art. This means the interference pattern can be obtained by using the common path configuration proposed in this first embodiment.

In the first embodiment, the light beams can be either polarized or un-polarized.

The illumination can consist of two beams, which come from the same light source and intersect on the sample with an angle between them. One beam is spatially filtered by the smaller pinhole on the spatial filter so the signal induced by the sample is removed. Such beam is called reference beam. Another beam is not spatially filtered since it goes through the larger pinhole on the spatial filter so the signal induced by the sample is not removed. Both beams are later combined on a digital camera with the intensity distribution governed by Eq. (5). By post processing the intensity distribution, or hologram, both phase and intensity images can be reconstructed using off-axis hologram algorithm. The algorithm mainly includes (1) reading the hologram into an array, (2) fast Fourier transforming the array, (3) bandpass filtering by setting everything to zero in the transformed array except on a circular disk centered on the first diffraction order. The radius of the disk is adjusted to that its perimeter is roughly midway between the zero and first diffraction orders, (4) inverse Fourier transforming the result in (3) to give the reconstructed complex amplitude "u", (5) In Matlab, the amplitude image is abs(u) and the phase image is angle(u), which is described in, for example, "Spatial Filtering for Zero-Order and Twin-Image Elimination in Digital Off-Axis Holography" Etienne Cuche, Pierre Marquet, and Christian Depeursinge, Applied Optics, Vol. 39, Issue 23, pp. 4070-4075 (2000).

The coherence length of the light source can be long (~several cm or longer, coherent light source) or short (~several microns or shorter, incoherent light source).

Using short coherence length light source can provide several desirable benefits, such as the possibility of using LEDs as light sources and minimizing the speckle problems associated with high coherent light sources. However, it may not be an easy task to use a low coherence length light source for the holographic microscopy with off-axis configuration. First, in order to use the low coherence length light source, the beam path lengths of object beam and reference beam need to be matched. Traditionally, unlike the common-path configuration proposed in the first embodiment, the object beam and reference beam are separated. Therefore, it is not easy to match the beam path lengths of reference and object beams. More fundamentally, the path length difference between the object beam and reference beam varies over the image of the field of view on the camera due to the object beam and reference beam having an angle not zero between them. This sets the fundamental lower limit for how short the coherence length can be. Interestingly, this fundamental limit can be overcome if the "phasefront" can be tilted relative to the wavefront (the plane perpendicular to the direction of the beam) such that the phasefronts of the object beam and reference beam on the camera are parallel.

The first embodiment solves both issues so a very low coherence length light source can be used. First, the beam path lengths are very matched since both object beam and reference beam go through the same optics. Second, the grating used to create both object beam and reference beam also tilts the phasefront relative to the wavefront such that the phasefronts of the object beam and reference beam on the camera are parallel even though the wavefronts of those two beams are not parallel. Therefore, the object beam and reference beam can interfere over the area of the field of view.

This described configuration can be used for the traditional holography. This configuration can also be used for microscopy with L1 as the objective lens and L2 as the tube lens.

The first embodiment provides two advantages: it does not affect the image angular contents in the Fourier plane and it can potentially be compact in size since the main additional component (spatial filter, SF, in FIG. 2) can be physically inside the existing imaging system for the traditional holography.

Those advantages can be very important when this configuration is implemented in microscopy. A typical microscope consists of an objective lens (L5 in FIG. 2), a tube lens (L6 in FIG. 2), and a camera. We note that the spatial filter (SF) is inside the existing microscope. Therefore, this configuration is physically compatible with typical microscopy without adding any physical length.

Figure 1:
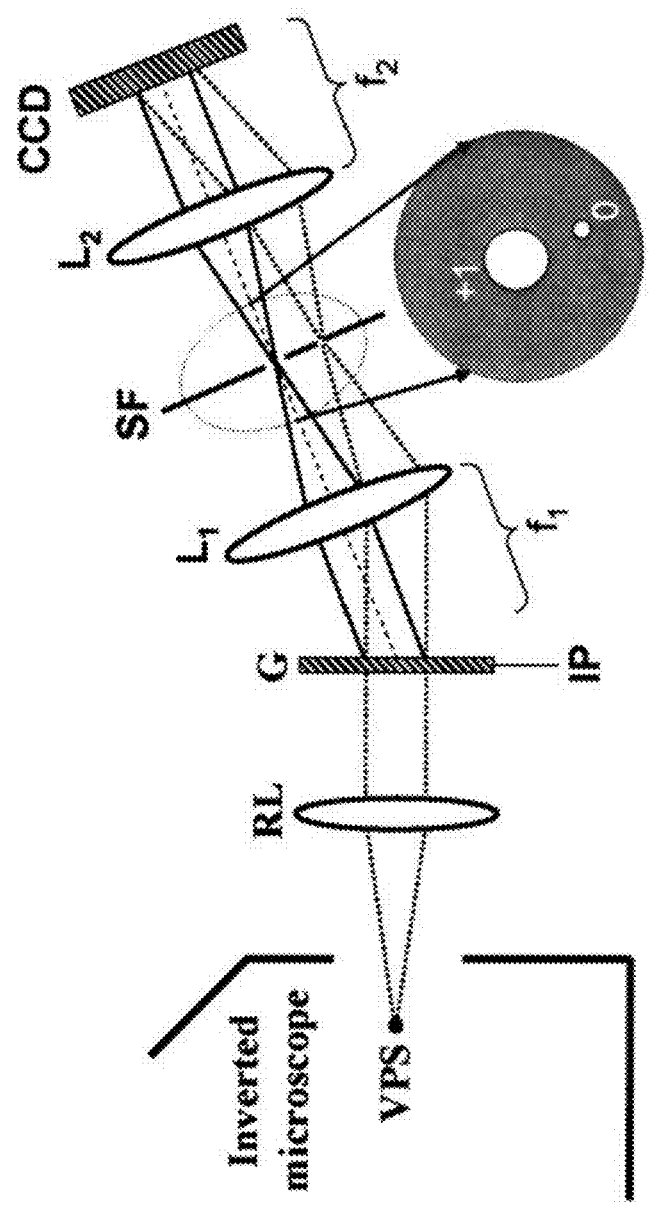
FIG. 1 illustrates an optical system of a related art.

On the other hand, the virtual source point VPS in FIG. 1 is the image formed on the output port of the microscope. In order to put a grating to split the image, a relay lens is used to form another image plane to create space for the grating in FIG. 1. After the grating in FIG. 1, another 4f relay lens system ($L_1$ and $L_2$) is used to achieve two things: (1) spatially filter the 0th-order beam to create a reference beam and (2) generate the final interferogram at the CCD plane.

Second Embodiment

In the first embodiment, the size of the big hole on the spatial filter 2010 can be limited by the adjacent smaller hole. Therefore, the angular contents which are allowed to go through might also be limited. This effectively may reduce the numerical aperture (NA) of the system. Thus, the resolution might be reduced.

Figure 3:
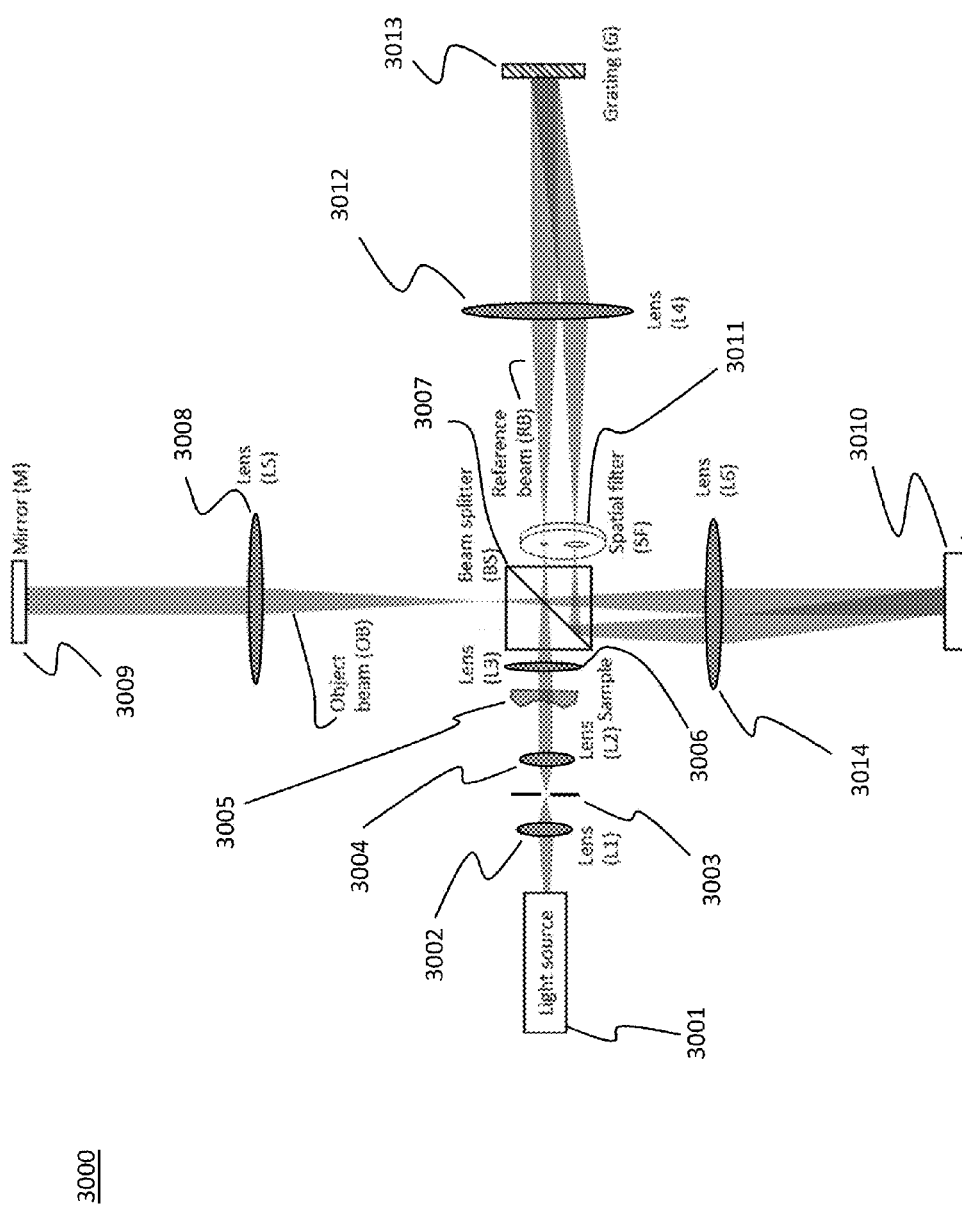
FIG. 3 illustrates an optical system of a second embodiment.

A diagram of an optical system 3000 for a holographic microscope, with common-path off-axis holography, is illustrated in FIG. 3. In this second embodiment, a single beam goes through a sample 3005, and then is split into reference and object beams.

The method provides two advantages: (1) it does not affect the image angular contents in the Fourier plane and (2) it can potentially be compact in size since the main additional components (a beam splitter, BS, and a spatial filter, SP, in FIG. 3) can be physically inside the existing imaging system for traditional holography.

Compared to the first embodiment, the main differences are: there is only a single beam going through the sample for this second embodiment. Whereas in the first embodiment, there are two beams going through the sample.

The object beam after the sample does not go through any more spatial filtering. Whereas in the first embodiment, there is a hole (the bigger hole on the spatial filter in FIG. 2) which may introduce unwanted spatial filtering.

In the diagram of the optical system for the common-path off-axis holography shown in FIG. 3, the light beam from a light source 3001 goes through a lens (L1) 3002 and a pinhole 3003 and is then collimated by the lens (L2) 3004, to form a plane wave. Unlike the first embodiment, one a single beam goes through the sample 3005. The light beam after the sample 3005 and a lens (L3) 3006 is split into two beams including a reference beam (RB) and object beam (OB).

Both the RB and OB have the spatial information about the sample 3005 after they go through the sample. However, when the RB goes through the spatial filter (SF) 3011, which is positioned at the Fourier plane, the sample information carried by the high spatial frequency components is blocked by the smaller pinhole of SF 3011 and only the DC component (DC component means spatially homogeneous light, such as a plane wave.) is through the pinhole of the size of the Airy diameter. Unlike the first embodiment (in which the OB goes through the bigger hole of SF 3011 on the spatial filter), the object beam does not go through any hole at all so there is no further spatial filtering for the OB which carries the information induced by the sample. The off-axis image hologram is recorded by the camera 3010 by the following configurations.

The object beam (OB) goes through a 4f relay lens system ((L3) 3006 and (L5) 3008) via beam splitter 3007 and forms an image of the sample 3005 on the mirror 3009 which is position on the image plane after the lens relay system. The image of the sample 3005 is further relayed onto the camera 3010 with another 4f relay lens system ((L5) 3008 and (L6) 3014).

The lenses (L3) 3006 and (L4) 3012 form a 4f relay lens system and the grating (G) 3013 is placed at a position of the image plane of the sample 3005. The reference beam (RB) is reflected from the grating (G) 3013 with an angle. The lenses (L4) 3012 and (L6) 3014 form another 4f relay lens system and the camera 3010 is placed at a position of the image plane of the grating 3013.

The RB and OB will be combined on substantially the same area on the camera 3010 to form an off-axis image hologram.

The intensity recorded on the camera 3010 is governed by the equations identical to the ones presented in the first embodiment.

Therefore, this second embodiment has all the benefits provided by the first embodiment.

The second embodiment affords two advantages: it does not affect the image angular contents in the Fourier plane and it can potentially be compact in size since the main additional components (beam splitter, BS, and spatial filter, SF, in FIG. 3) can be physically inside the existing imaging system for the traditional holography.

Those advantages can be very important when this configuration is implemented in microscopy. A typical microscope consists of an object lens (L3) 3006 in FIG. 3, a tube lens ((L5) 3008 in FIG. 3), and a camera 3010. Note that the both the BS and SF are inside the existing microscope. Therefore, this configuration is physically compatible with typical microscopy without adding any physical length.

The second embodiment also provides one advantage over the first embodiment: the numerical aperture is not limited due to spatial filtering of the object beam. Therefore, the resolution of this invention can be better than that with the first embodiment.

Third Embodiment

Figure 4A:
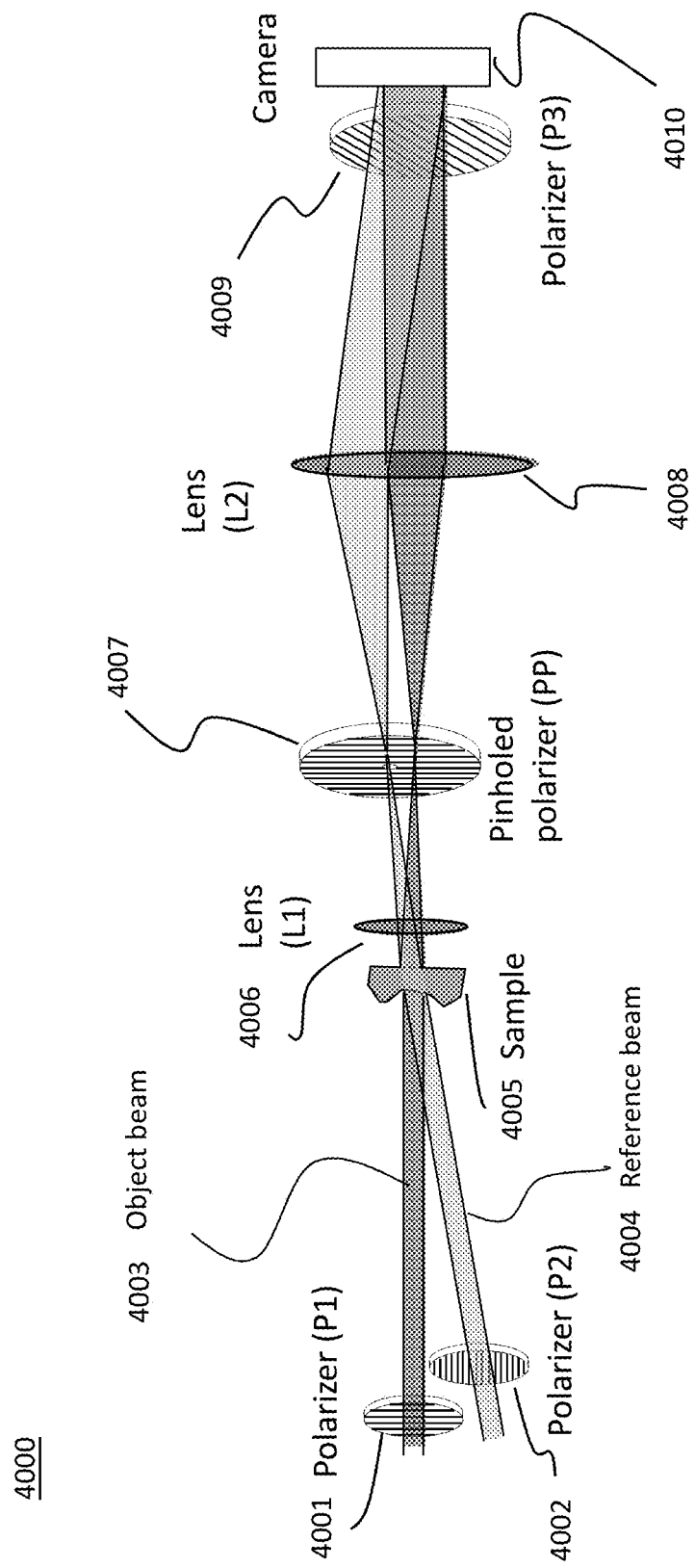
FIGS. 4A and 4B illustrate an optical system of a third embodiment.

In the third embodiment, another optical system 4000 for off-axis holography is illustrated in FIG. 4A. The optical system uses polarization.

In traditional holography, two beams are required. One is the reference beam which does not go through the sample. Another one is the object beam which goes through the sample so it carries the information induced by the sample. Usually, two beams are separated using a beam splitter and the reference beam and object beam are set up similarly along two different light paths. The drawback for this type of arrangement is that the two light paths may experience different disturbance which causes noise on the holograms. Another significant shortcoming is for implementing holography in microscopy.

Figure 4B:
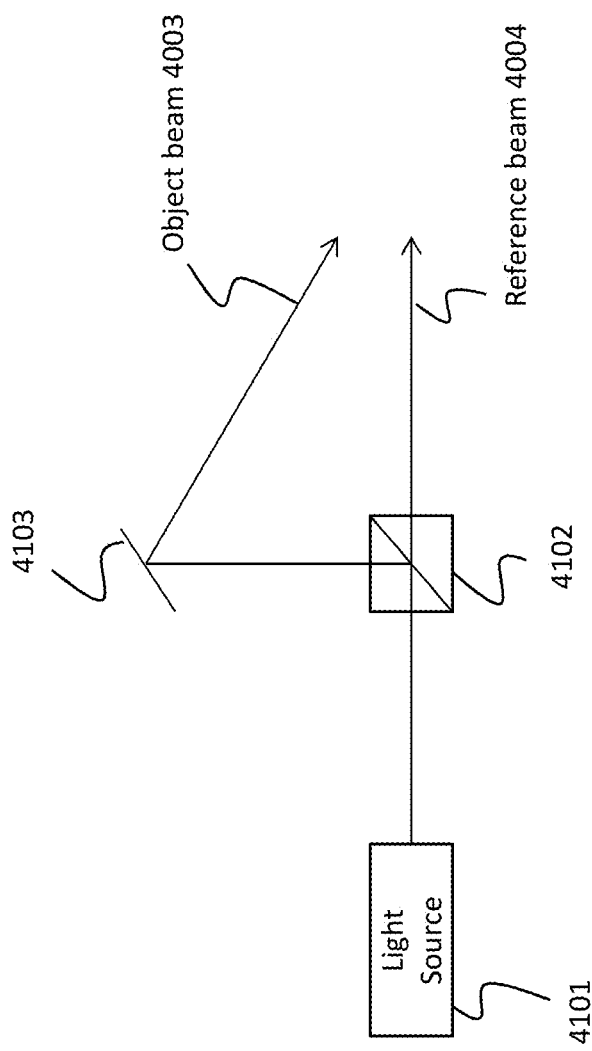

A diagram of the third embodiment, with common-path off-axis interferometer using polarization, is illustrated in FIGS. 4A and 4B. A beam emitted from a light source 4101 in FIG. 4B is split into two beams by a beam splitter 4102. The two beams (reference beam 4004 and object beam 4003) are split from the same light source 4101 so they have the same light wavelength characteristic. The object beam 4003 is reflected by a mirror 4103. The reference beam 4004 goes through a Polarizer (P2) 4002, and the object beam 4003 goes through a Polarizer (P1) 4001, as illustrated in FIG. 4A.

The polarizations of those two beams can be perpendicular to each other. They go through the sample 4005 in the same area but with different angles. Two lenses (L1) 4006 and (L2) 4008 form a 4-f relay lens system which images the sample 4005 onto the camera 4010. Both the reference beam 4004 and object beam 4003 have the spatial information about the sample after they go through the sample. However, when the reference beam 4004 goes through the pinholed polarizer (PP) 4007, which is positioned at the Fourier plane, the sample information carried by the high spatial frequency components of the reference beam 4004 is blocked by the PP 4007 and only the DC component is through the PP 4007 with a pinhole size of the Airy diameter. (DC component means spatially homogeneous light, such as a plane wave.)

A polarizer (P3) 4009 can be used for two purposes: 1. Before P3, the reference and object beams have polarizations perpendicular to each other. After the polarizer (P3) 4009, the polarizations of two beams are realigned to be parallel so they can interfere. 2. The orientation of the polarizer (P3) 4009 will control the throughputs of the reference and object beams so it can be used to balance the intensities of these two beams to improve the contrast ratio of the interference.

Electric fields for an object beam, $E_O(x,y)$, and a reference beam, $E_R(x,y)$, after the sample can be written as follows:

$$E_O(x,y)=E_y(x,y)\exp[i\phi(x,y)]$$

$$E_R(x,y)=E_x(x,y)\exp[i(\phi(x,y)+\beta y)] \quad (7)$$

Polarization states for both beams are Y and X linearly polarized light respectively. β is a coefficient corresponding to an off-axis angle. After the pinholed polarizer (PP) 4007, the electric fields can be written as follows:

$$E_O(x,y)=E_y(x,y)\exp[i\phi(x,y)]$$

$$E_R(x,y)=E_x\exp[i(\beta y+\phi(0,0))] \quad (8)$$

After the last polarizer, electric fields can be written as follows:

$$E_O(x, y) = \frac{E_y(x, y)}{\sqrt{2}}\exp[i\phi(x, y)] \quad (9)$$

$$E_R(x, y) = \frac{E_x}{\sqrt{2}}\exp[i(\beta y + \phi(0, 0))]$$

Both fields have the same linear polarization defined by the last polarizer. Thus, when two beams are recombined on the camera, the light intensity on the detector is expressed as $$|E_O(x,y)+E_R(x,y)|^2=|E_O(x,y)|^2+|E_R(x,y)|^2+E_O(x,y)E_R^*(x,y)+E_O^*(x,y)E_R(x,y) \quad (10)$$

where the first and second terms correspond to 0th order light, and the third term corresponds to +1st order light, and the fourth term corresponds to −1st order light. The sample information is recorded in the +1st and −1st order lights.

The third and fourth terms, which are important part for intensity on the detector, can be re-written as follows.

$$E_O(x, y)E_R^* + E_O^*(x, y)E_R = \quad (11)$$
$$\frac{|E_Y(x, y)||E_X|}{2}(\exp[i(\phi(x, y) - \beta y - \phi(0, 0))] +$$
$$\exp[-i(\phi_O(x, y) - \beta y - \phi(0, 0))]) =$$
$$|E_Y(x, y)||E_X|\cos(\phi(x, y) - \beta y - \phi(0, 0))$$

Moreover, the same distribution can be obtained by calculating a real part of the third term.

We note that Eq. (11) is basically the same as the cross term, $|E_O||E_1(x,y)|\cos[\phi(x,y)-\beta(x+y)-\phi_0]$, in the prior art described above. This means the interference pattern can be obtained by using the common path system proposed in this embodiment. This embodiment can substantially use a whole area of an objective lens aperture for the object beam. Then, this embodiment can use a full NA of the objective lens to generate hologram, which means that it can obtain a higher resolution.

General samples may have a variety of spatial frequency, so a lot of scattered angles from the sample are expected. Then, the incident object beam and the incident reference beam can be parallel to each other. This makes an experimental setup be much simpler.

However, a high intensity for the reference beam might not be obtained at the pinhole position always. Then, an intensity ratio between the incident object beam and the incident reference beam can be compensated, in order to obtain a high contrast on the detector.

If a sample is similar to a sinusoidal grating, a blazed grating or any other special cases, a high intensity for reference beam cannot be expected. Then, the angle between two beams can be compensated, in order to obtain a high contrast on the detector. One case for this technique might be that the angle is zero above.

The third embodiment can provide three advantages: it does not affect the image angular contents in the Fourier plane and it can potentially be compact in size since the main additional components (pinholed polarizer and polarizer, P3, in FIG. 4) can be physically inside the existing imaging system for traditional holography.

It uses the full NA of the objective lens to generate hologram, which means that it can obtain a higher resolution.

Those advantages can be very important when this configuration is implemented in microscopy. A typical microscope consists of an object lens ((L1) 4006 in FIG. 4), a tube lens ((L2) 4008 in FIG. 4), and a camera 4010. Note that the pinholed polarizer 4007 and the polarizer (P3) 4009 are both inside the existing microscope. Therefore, this configuration is physically compatible with typical microscopy without adding any physical length.

Fourth Embodiment

The general samples may have a lot of spatial frequencies, and they can generate a lot of scattered light by applying a plane wave incident light. This means that the general samples can have a kind of function of gratings. However, the configuration in the described prior art requires the grating all the time. The reference beam in the above described prior art goes through the sample, so a spectrum for the reference will be the same as one for the object beam. Then, all reference spectrums except for the center are cut by the spatial filter. Therefore, the energy ratio between the object beam and the reference beam can be changed. As a result, a contrast in holograms might be low. In order to obtain a high contrast, the energy of the object beam and the energy of the reference beam in the detector should be similar to each other.

In the fourth embodiment, a simple configuration will be presented. An optical system 5000 doesn't include the grating on the sample 5001 or an image plane of the sample. Also, another configuration for obtaining a high contrast in holograms will be explained. The contrast will be controlled by changing the direction of a linear polarized light as an incident light.

Figure 5:
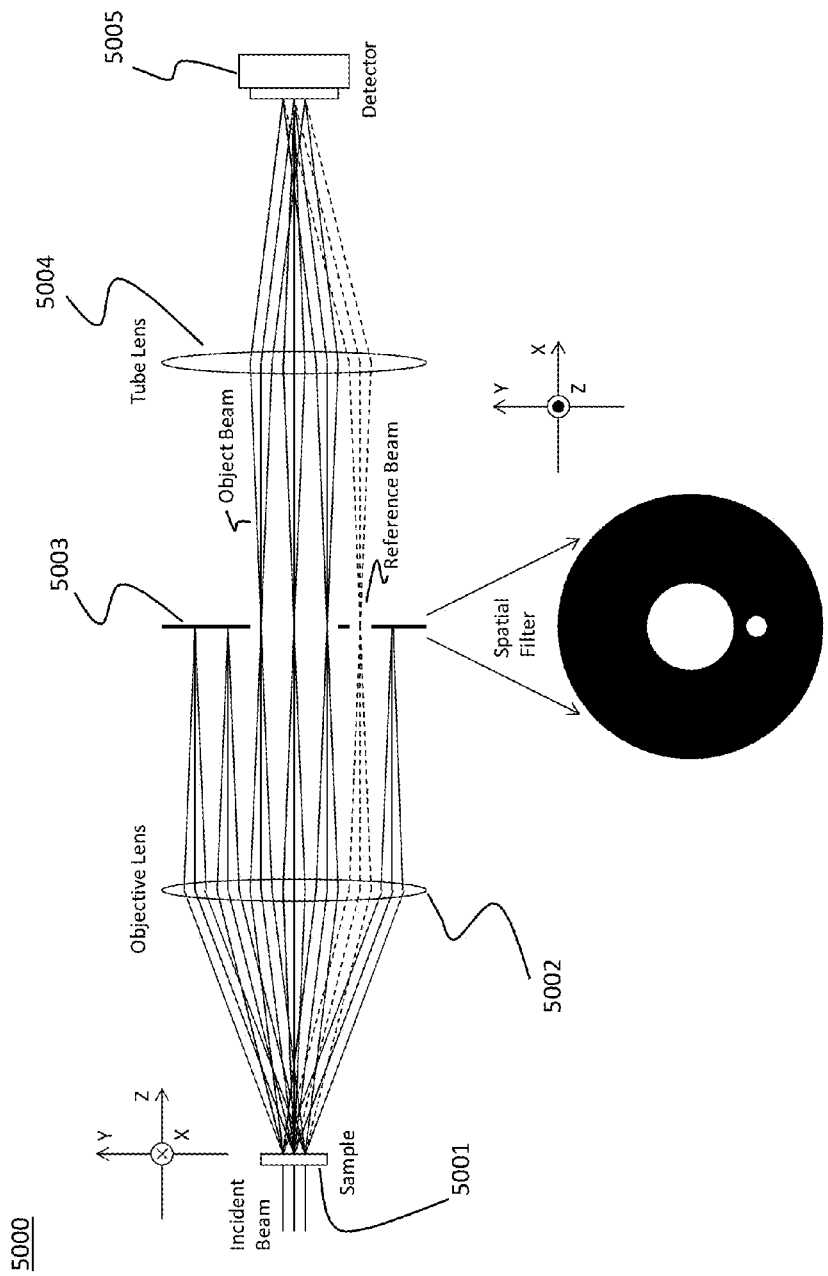
FIG. 5 illustrates an optical system of a fourth embodiment.

FIG. 5 shows a basic system configuration 5000 for the fourth embodiment. There is no grating on the sample even if the incident beam is single, which means an object and reference beam are integrated into one beam. A spatial filter 5003 is on a focus plane of objective lens 5002. The filter 5003 has a large hole in the center so that an object beam can go through the filter 5003. The filter 5003 has another tiny hole in the outside of the hole for the object beam so that the center spectrum of a reference beam can go through the filter. Two lenses (Objective lens) 5002 and (Tube lens) 5004 form a 4-f relay lens system which images the sample 5001 onto the camera 5005.

Electric fields for an object beam, $E_O(x,y)$, and a reference beam, $E_R(x,y)$, after the sample can be written as follows:

$$E_O(x,y)=E(x,y)\exp[i\phi(x,y)]$$

$$E_R(x,y)=E(x,y)\exp[i\phi(x,y)] \quad (12)$$

After the spatial filter, the electric fields can be written as follows:

$$E_O(x, y) = E(x, y)\exp[i\phi(x, y)] \quad (13)$$

$$E_R(x, y) = \frac{\tilde{E}(0, \eta_0)}{\int \tilde{E}(\xi, \eta)d\xi d\eta}\exp[i(\beta y + \phi(0, 0))]$$

$\tilde{E}$ is the spectrum of $E_O$ and $E_R$ in equation 12, which is calculated by Fourier transform. When two beams are recombined on the camera, the light intensity on the detector is expressed as $$|E_O(x,y)+E_R(x,y)|^2 = |E_O(x,y)|^2+E_R(x,y)|^2+E_O(x,y)E_R^*(x,y)+E_O^*(x,y)E_R(x,y) \quad (14)$$

where the first and second terms correspond to 0th order light, and the third term corresponds to +1st order light, and the fourth term corresponds to −1st order light. The sample information is recorded in the +1st and −1st order lights. In order to obtain a high contrast in holograms, amplitudes (a square route of energy) for the object and reference beams should be the same or quite similar to each other. The method to obtain the same amplitude will be explained below.

Figure 6:
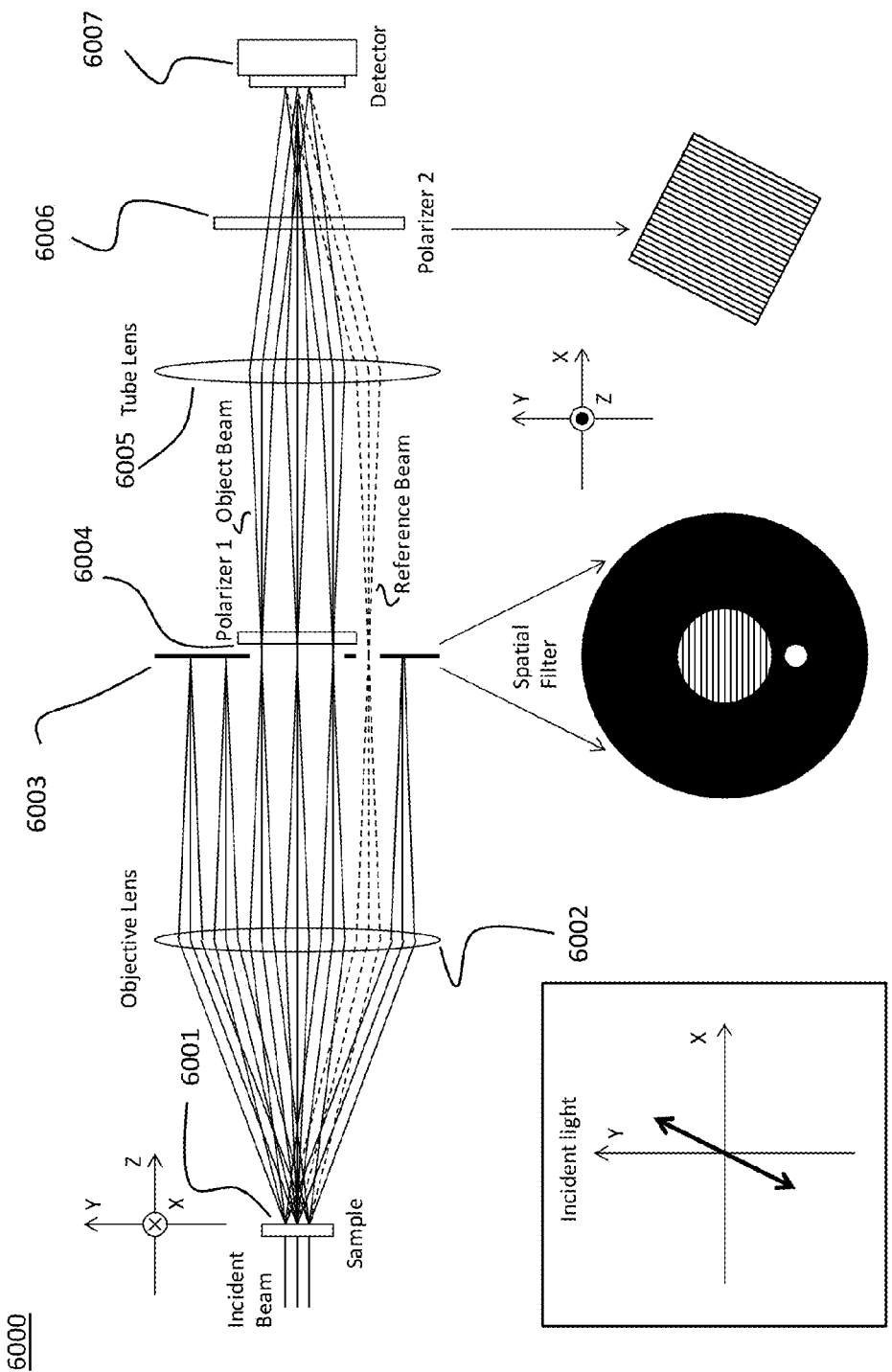
FIG. 6 illustrates an optical system related to the fourth embodiment.

FIG. 6 illustrates a system configuration 6000 consisting of polarizers 6004, 6006 to obtain a high contrast in holograms. An incident beam is the linearly polarized light as shown in a square of FIG. 6, and the beam travels from the sample 6001 to a spatial filter 6003 via an objective lens 6002. The first polarizer (Polarizer 1) 6004 is located at the hole for the object beam in the filter. The polarizer 6004 is along x-direction in this embodiment, so the x-polarized light for the object beam can go through the filter 6003. The second polarizer (Polarizer 2) 6006 is located at between a tube lens 6005 and a detector 6007 in order to modify the amplitude of the object beam.

By changing the polarization direction of the incident beam and the direction of the second polarizer 6006, the amplitude of the object beam can be modified. When both angles are the same, the energy of the incident light might be used efficiently. The angle of the polarization direction of the incident beam might be rotated by using a half wave plate.

Figure 7C:
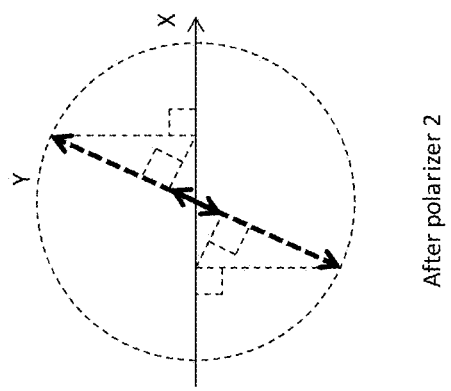
FIGS. 7A, 7B and 7C illustrate electric fields for object and reference beams.
Figure 7B:
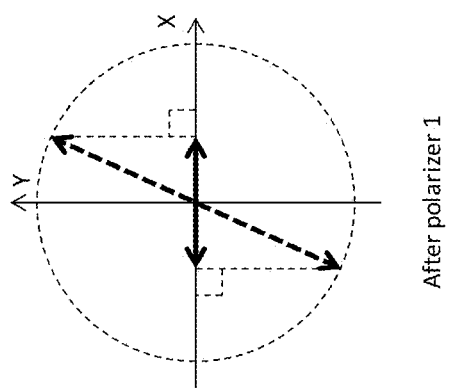
Figure 7A:
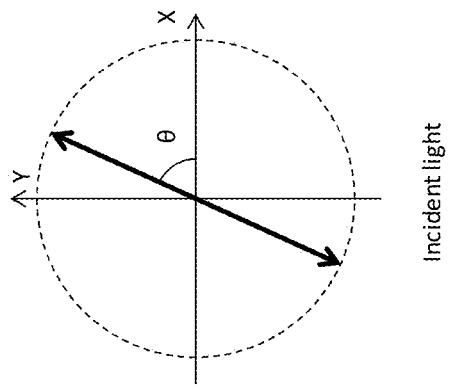

FIGS. 7A, 7B, and 7C illustrate electric fields for the object and reference beams in each position. The solid line indicates the amplitude of the object beam, and the dotted line indicates the amplitude of the reference beam. As shown in FIG. 7A, In the incident light, both amplitudes are the same (FIG. 7A). After the first polarizer 6004, the amplitude for the object beam is modified as cos θ times smaller (FIG. 7B). After the second polarizer 6006, one is modified as $\cos^2\theta$ times smaller (FIG. 7C). The energy is modified as $\cos^4\theta$ times smaller after the second polarizer.

After the spatial filter in this configuration with polarizers, the electric fields can be written as follows:

$$E_O(x, y) = \frac{E(x, y)}{\cos^2\theta} \exp[i\phi(x, y)] \qquad (15)$$

$$E_R(x, y) = \frac{\tilde{E}(0, \eta_0)}{\int \tilde{E}(\xi, \eta) d\xi d\eta} \exp[i(\beta y + \phi(0, 0))]$$

When the angle θ satisfies the following relationship, $$\frac{\int E(x, y) dx dy}{\cos^2\theta} = \frac{\tilde{E}(0, \eta_0)}{\int \tilde{E}(\xi, \eta) d\xi d\eta} \qquad (16)$$

the third and fourth terms in equation (14), which are important part for intensity on the detector, can be re-written as follows.

$$E_O(x, y)E_R^* + E_O^*(x, y)E_R = \qquad (17)$$

$$\left| \frac{E(x, y)}{\cos^2\theta} \right| \left| \frac{\tilde{E}(0, \eta_0)}{\int \tilde{E}(\xi, \eta) d\xi d\eta} \right| (\exp[i(\phi(x, y) - \beta y - \phi(0, 0))] +$$

$$\exp[-i(\phi_O(x, y) - \beta y - \phi(0, 0))]) =$$

$$2 \left| \frac{E(x, y)}{\cos^2\theta} \right| \left| \frac{\tilde{E}(0, \eta_0)}{\int \tilde{E}(\xi, \eta) d\xi d\eta} \right| \cos(\phi(x, y) - \beta y - \phi(0, 0))$$

Moreover, the same distribution can be obtained by calculating a real part of the third term.

Nte that Eq. (17) is basically the same as the cross term, $|E_O||E_1(x,y)|\cos[\phi(x,y)-\beta(x+y)-\phi 0]$, in the prior art. This means the interference pattern can be obtained by using the common path configuration proposed in this embodiment.

The fourth embodiment depends on the fact that the objects generate a lot of scattered light by applying a plane wave incident light. However the objects might be too weak as scattering objects, the amplitude for the reference beam might be small, and another support might be expected. The method to support to increase the amplitude for the reference light will be explained below.

Figure 8:
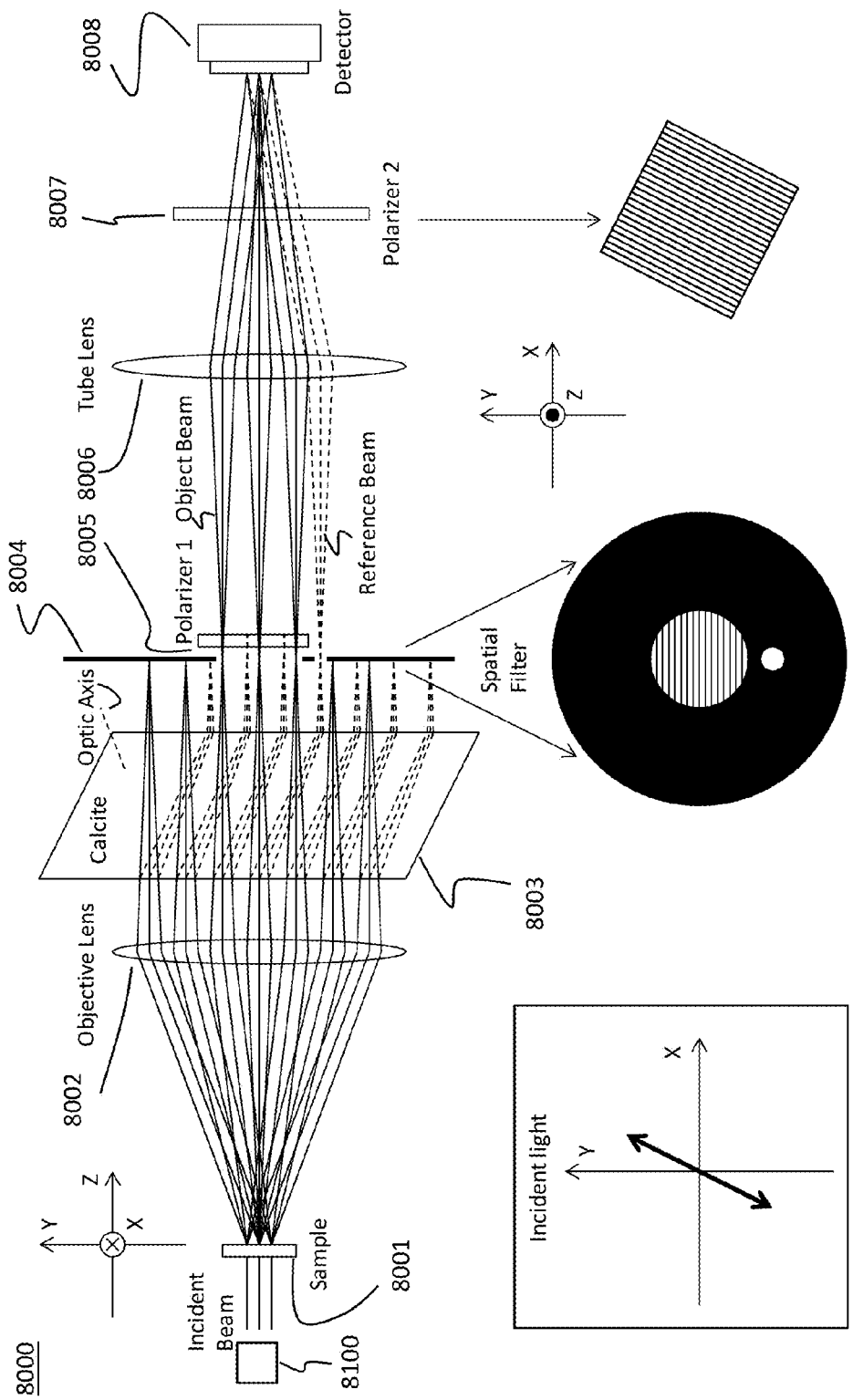
FIG. 8 illustrates an optical system related to the fourth embodiment.

A system configuration consisting of a birefringence material to obtain a high contrast in holograms is illustrated in FIG. 8. An incident beam is the linearly polarized light as shown in a square of FIG. 8. In this embodiment, calcite 8003 is used as a birefringence material. When the optic axis of the calcite crystal is set in y-z plane, y-polarization is refracted, but x-polarization is not refracted. As a result, only the reference beam can be shifted. An incident beam, emitted from a light source 8100, irradiates a sample 8001, and then is led to the calcite 8003 via an objective lens 8002. A spatial filter 8004, a polarizer 8005, a tube lens 8006, a polarizer 8007, and a detector 8008 work as described with reference to FIG. 6.

In FIG. 8, 0th order light for the reference beam is shifted into the center of the second hole. However this perfect shift amount is not required. Even if one is shifted a little bit, e.g. a quarter or half amount, the amplitude for the reference beam will be modified. Also, the energy ratio between the object and reference beam can be controlled by changing the angle of the polarization direction of the incident beam, or the direction of the second polarizer, or both of them.

In this embodiment, the calcite 8003 is located between the objective lens 8002 and the filter 8004, but one can be located at anywhere, e.g., between the sample 8001 and the objective lens 8002.

As described above, a system 8000 for digital holographic microscopy with an aperture (filter 8004), which has the first hole for an object beam in the center and the second tiny hole in the outside of the first one, can be provided.

The system configuration can be simpler. The system doesn't include the grating on sample or the image plane of the sample. The system configuration with polarizers can obtain a high contrast in holograms by changing the direction of a linear polarized light as an incident light.

Fifth Embodiment

Figure 9:
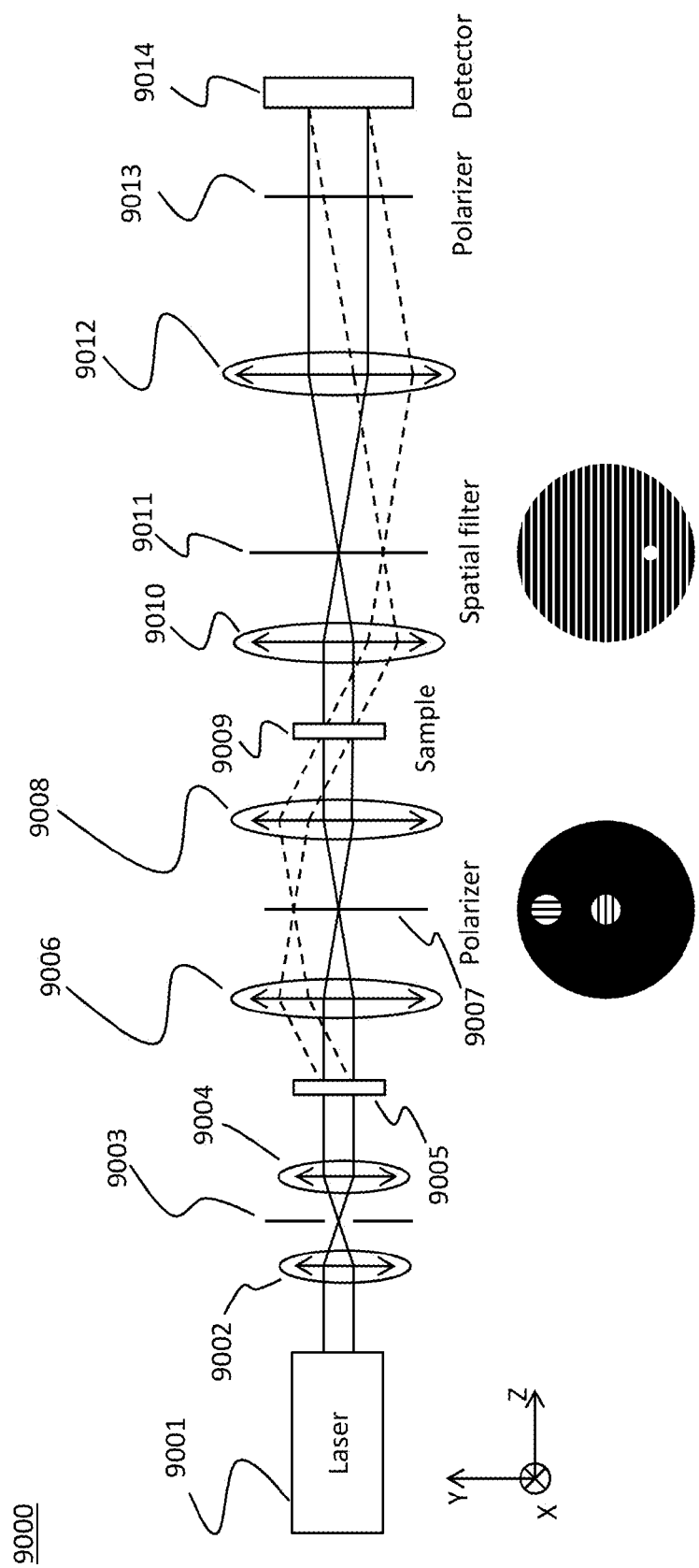
FIG. 9 illustrates an optical system of a fifth embodiment.

Another optical system 9000 is illustrated in FIG. 9. The system configuration includes a grating 9005, lenses 9002, 9004, 9006, 9008, 9010 and 9012, slit 9003, polarizers 9007, 9011 and 9013, and dual incident beams to the sample 9009. The beam emitted from the laser source 9001 is separated into two beams by the grating 9005. One is for the object beam (solid line), and the other is for the reference beam (dotted line). Lenses 9002, 9004, and a slit 9003 are used. The polarizer 9007 makes the object beam being x polarization and the reference beam being y polarization. Both beams go through the sample 9009, and both are diffracted by the sample 9009. The spatial filter 9011 allows the diffracted light of the object beam to go through without any modification. The spatial filter 9011 cuts all diffracted light of the reference beam except for 0th order light. After the spatial filter 9011, the reference beam becomes plane wave traveling to a polarizer 9013 via a lens 9012. The polarizer 9013 makes both beams being interfered, so a fringe pattern as a hologram is observed in the detector 9014.

Sixth Embodiment

Figure 10:
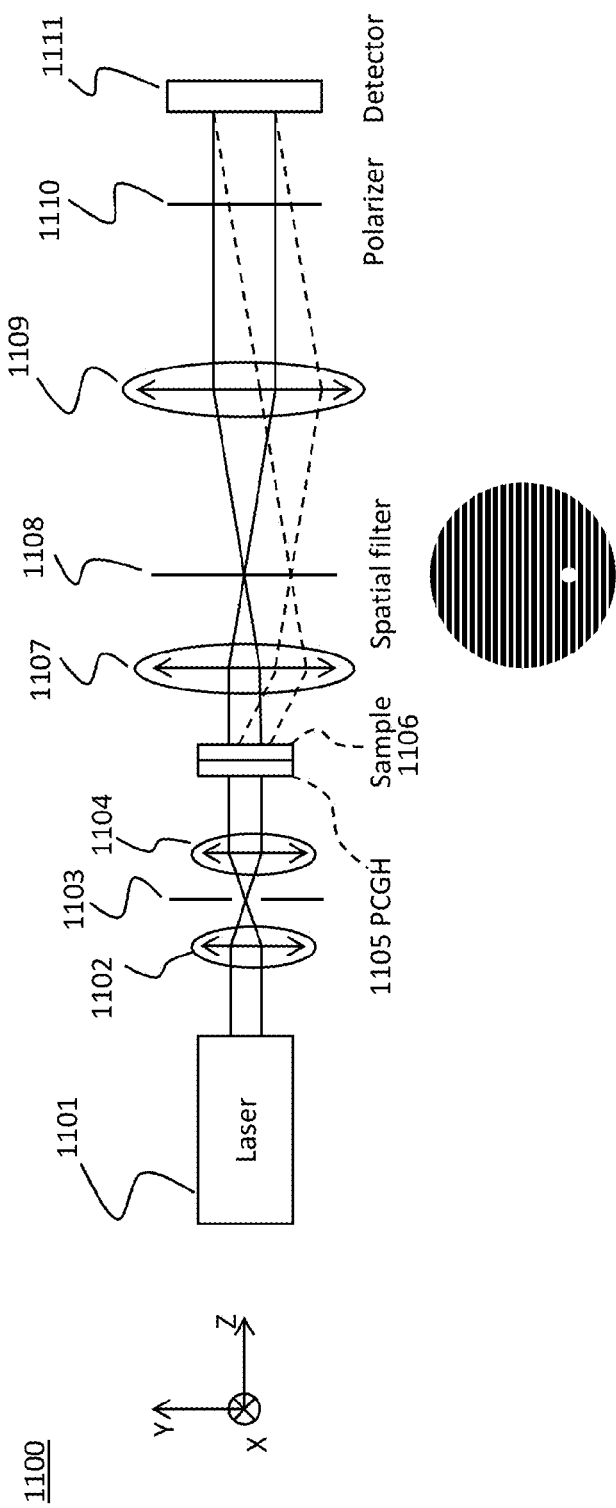
FIG. 10 illustrates an optical system of a sixth embodiment.

Another optical system 1100 is illustrated in FIG. 10. The system configuration 1100 includes a polarization sensitive computer generated hologram (PCGH) 1105, polarizers 1108 and 1110, and single incident beam to the sample 1106. The beam emitted from the laser source 1101 is separated into two beams by the PCGH 1105 via a lens 1102, a slit 1103, and a lens 1104. One is for the object beam (solid line), and the other is for the reference beam (dotted line). After the sample 1106, the configuration is the same as the fifth embodiment. Via a lens 1107, a spatial filter 1108, a lens 1109, and a polarizer 1110, the reference and object beams are combined on a detector 1111.

Figure 11:
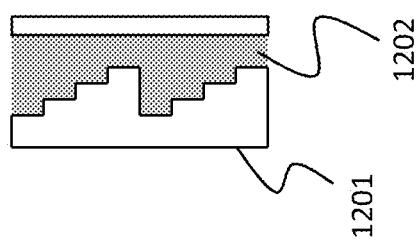
FIG. 11 illustrates an example of polarization sensitive computer generated hologram (PCGH) used in the sixth embodiment.

The PCGH 1105 is described in detail here. One example of PCGH 1105 is illustrated in FIG. 11. The PCGH 1105 consists of blazed shape grating made of birefringent material 1201 and oil 1202. The refractive index for the birefringent material along x axis is the same as the oil refractive index (n=1.49). The index of the birefringent material is 1.49 along x axis and 1.66 along y axis. Therefore the PCGH 1105 behaves like a plane glass plate for x polarization, and is like a grating for y polarization. Then x polarization as the object beam goes through the PCGH 1105, and y polarization as the reference beam is bent as a diffraction effect.

While the embodiments according to the present invention have been described with reference to exemplary embodiments, it is to be understood that the present invention is not limited to the above described embodiments. The scope of the following claims is to be accorded the broadest interpretation so as to encompass all such modifications and equivalent structures and functions.

What is claimed is:

1. An optical system for a holographic microscope comprising:
   a light source configured to emit a light beam;
   a grating configured to split the light beam into a reference beam and an object beam, the reference beam being a beam bent by the grating, and the object beam being a beam which goes straight through the grating;
   a first polarizer configured to make the reference beam and the object beam be polarized differently from each other;
   wherein, the grating and the first polarizer are positioned such that a sample is irradiated by both the reference beam and the object beam split by the grating and polarized by the first polarizer;
   a spatial filter made up of a second polarizer and a pinhole, the pinhole being provided at a position distant from a center of the spatial filter;
   wherein the object beam from the sample passes the second polarizer and the pinhole, and the reference beam from the sample passes the pinhole and does not pass through the second polarizer; and
   a detector configured to detect an interference pattern caused by the reference beam after it has passed through the pinhole and the object beam after it has passed through the second polarizer and the pinhole.

2. The optical system for the holographic microscope according to claim 1, further comprising one more lenses between the grating and the sample.

3. The optical system for the holographic microscope according to claim 1, wherein:
   the light source is a low coherence length light source; and
   a phasefront of the object beam is parallel to a phasefront of the reference beam at the detector.

4. The optical system for the holographic microscope according to claim 3, wherein the phasefront of the object beam is tilted relative to a wavefront of the object beam.

5. The optical system for the holographic microscope according to claim 4, wherein the phasefront of the object beam is tilted relative to a wavefront of the object beam by the grating.

6. The optical system for the holographic microscope according to claim 3, wherein the phasefront of the reference beam is tilted relative to a wavefront of the reference beam.

7. The optical system for the holographic microscope according to claim 6, wherein the phasefront of the reference beam is tilted relative to a wavefront of the reference beam by the grating.

8. The optical system for the holographic microscope according to claim 3, wherein the phasefronts of the object beam and the reference beam are tilted relative to wavefronts of the object beam and the reference beam.

9. The optical system for the holographic microscope according to claim 8, wherein the phasefronts of the object beam and the reference beam are tilted relative to wavefronts of the object beam and the reference beam by the grating.

10. The optical system for the holographic microscope according to claim 1, further comprising a 4-f relay lens system which images the sample onto the detector.

11. The optical system for the holographic microscope according to claim 1, wherein the pinhole transmits only 0th order light.

12. The optical system for the holographic microscope according to claim 1, wherein the first polarizer makes the object beam and the reference beam be polarized perpendicular to each other.

13. The optical system for the holographic microscope according to claim 1,
    wherein the grating, the first polarizer, and the spatial filter are arranged in this order in a direction of the light beam from the light source to the detector, and
    the grating is arranged at a conjugated position of the sample, and the first polarizer and the spatial filter are arranged at a conjugated position with each other.

14. An optical system for a holographic microscope comprising:
    a light source configured to emit a light beam;
    a grating configured to split the light beam into a reference beam and an object beam, the reference beam being a beam bent by the grating, and the object beam being a beam which goes straight through the grating;
    a first polarizer configured to make the reference beam and the object beam be polarized differently from each other;
    wherein, the grating and the first polarizer are positioned such that a sample is irradiated by both the reference beam and the object beam split by the grating and polarized by the first polarizer, wherein the grating is arranged at a conjugated position of the sample;
    a spatial filter made up of a second polarizer and a pinhole, the pinhole being provided at a position distant from a center of the spatial filter, wherein the first polarizer and the spatial filter are arranged at a conjugated position with each other;
    wherein the object beam from the sample passes the second polarizer and the pinhole, and the reference beam from the sample passes the pinhole and does not pass through the second polarizer; and
    a detector configured to detect an interference pattern caused by the reference beam after it has passed through the pinhole and the object beam after it has passed through the second polarizer and the pinhole; and
    wherein the grating, the first polarizer, and the spatial filter are arranged in this order in a direction of the light beam from the light source to the detector.

* * * * *